US008642096B2

(12) United States Patent
Auh et al.

(10) Patent No.: US 8,642,096 B2
(45) Date of Patent: Feb. 4, 2014

(54) PHARMACEUTICAL COMPOSITION CONTAINING HERBAL EXTRACT FOR PREVENTION OR TREATMENT OF NEPHRITIS (75) Inventors: Jin Auh, Seoul (KR); Chang-Hwan Kim, Hwaseong-si (KR); Chang-Kyun Han, Seoul (KR); Sung-Hum Yeon, Suwon (KR); Seung-In Choe, Seoul (KR); Young-June Shin, Gimhae (KR); Dong-Oh Han, Anyang (KR); Soo-Im Chang, Suwon (KR); Ji-Hye Lee, Ansan (KR); Jun-Seok Lee, Suwon (KR); Ho-Young Kwak, Suwon (KR); Hyo-Jin Moon, Suwon (KR); Jong-Wook Lee, Suwon (KR); Sung-Min Kim, Suwon (KR)

(73) Assignee: Ahn-Gook Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 13/375,255

(22) PCT Filed: Jun. 1, 2010

(86) PCT No.: PCT/KR2010/003530
§ 371 (c)(1),
(2), (4) Date: Nov. 30, 2011

(87) PCT Pub. No.: WO2010/140832
PCT Pub. Date: Dec. 9, 2010

(65) Prior Publication Data
US 2012/0070517 A1     Mar. 22, 2012

(30) Foreign Application Priority Data
Jun. 4, 2009    (KR) .................. 10-2009-0049626

(51) Int. Cl.
*A01N 65/00*    (2009.01)
(52) U.S. Cl.
USPC ......................................................... 424/725
(58) Field of Classification Search
None
See application file for complete search history.

(56) References Cited

U.S. PATENT DOCUMENTS

| 2002/0127285 A1 | 9/2002 | Xiu |
| 2004/0258740 A1 | 12/2004 | Thompson |
| 2008/0118584 A1 | 5/2008 | Rangel |

FOREIGN PATENT DOCUMENTS

| CN | 1565520 | 1/2005 |
| CN | 1943761 | 4/2007 |
| CN | 101167802 | 4/2008 |
| CN | 101530469 | 9/2009 |
| EP | 1880719 | 1/2008 |
| JP | 2000-159673 | 6/2000 |
| KR | 10-1999-0014646 | 2/1999 |
| KR | 2001018668 | * 3/2001 |
| KR | 10-2001-0096623 | 11/2001 |
| KR | 10-2003-0029563 | 4/2003 |
| KR | 2003085250 | * 11/2003 |
| KR | 10-2004-0058526 | 7/2004 |
| KR | 10-0516194 | 9/2005 |
| WO | 2007/109804 | 9/2007 |

OTHER PUBLICATIONS

Web MD, "Find a Vitamin or Supplement-Hawthorn", 4 pages, 2009.*
Hyuck-Jai Choi, "Inhibitory Effects of Crude Drugs on a-Glucosidase", Arch Pharm Res vol. 23, No. 3, 261-266, 2000.
Lei zhen jia et al., "Initial observation on treatment effect of 105 cases suffering from pyelonephritis using Hawthorn extract,"Xhanxi New medicine, vol. 1, pp. 35-37, 1975.
Yan zhao, Study on Anatomical Structure, Biomass and Antibiotic of Equisetum in Shanxi, Shanxi Univerisity Doctoral dissertation, vol. 6, 2008.
Sivakmnar J. T. Gowder et al. "Effect of the Food Flavour Cinnamaldehyde on the Antioxidant Status of Rat Kidney," Basic & Clinical Pharmacology & Toxicology, 99, 379-382 (Nov. 2006).
Xiao Jin-zhu etc. "Effects of extracts from Prunella vulgaris on osteopontin expression in renal tissue of urolithiasis model rats with calcium oxalate stone," China Journal of Modern Medicine, vol. 18, No. 81005-8982, 08-1013-05 (Apr. 2008).
Nagai H et al: "Immunopharmacological studies of the aqueous extract of Cinnamomum cassia (CCAq). II, Effect of CCAq on experimental glomerulonephritis" Japanese Journal of Pharmacology 1982 JP, vol. 32. No. 5, pp. 823-831, ISSN: 0021-5198 (Oct. 1982).
Park E Y et al: "Antioxidant and Anti-inflammatory Activities of Equisetum hyemale", Natural Product Sciences, Korean Society of Pharmaconosy, Seoul, KR, vol. 14, No. 4, pp. 239-243, XP009172443, ISSN:1226-3907 (Dec. 1, 2008).
European Patent Office, The extended European search report for EP 10783581.1 (Sep. 27, 2013).

* cited by examiner

*Primary Examiner* — Michael Meller
(74) *Attorney, Agent, or Firm* — Lexyoume IP Meister, PLLC.

(57) ABSTRACT

The present invention relates to a novel use of herbal extracts in a pharmaceutical composition for prevention and treatment of nephritis and, more particularly, to a pharmaceutical composition and a health functional food for prevention and/or treatment of nephritis that contains at least one herbal extract selected from the group consisting of a Crataegi Fructus extract, a Cinnamomi Cortex extract, a Prunella Spica extract, and an Equiseti Herba extract, a method for prevention and/or treatment of nephritis using the herbal extract, and a use of the herbal extract in preparation of a composition for prevention and/or treatment of nephritis. The herbal extract has a good therapeutic effect for nephritis on a nephritis model of which the nephritis is induced by a drug such as gentamicin, cisplatin, etc., and a good inhibitory activity on the growth of mesangial cells in kidneys, thereby providing a very useful means for prevention and/or treatment of nephritis.

6 Claims, 4 Drawing Sheets

(a) NORMAL (b) NEGATIVE CONTROL (c) TEST

PHARMACEUTICAL COMPOSITION CONTAINING HERBAL EXTRACT FOR PREVENTION OR TREATMENT OF NEPHRITIS

FIELD OF THE INVENTION

The present invention relates to a pharmaceutical composition and a health functional food for prevention and/or treatment of nephritis, which comprise at least one herbal extract selected from the group consisting of a Crataegi Fructus extract, a Cinnamomi Cortex extract, a Prunella Spica extract, and an Equiseti Herba extract, a method for prevention and/or treatment of nephritis using the herbal extract, and a use of the herbal extract in preparation of a composition for prevention and/or treatment of nephritis.

BACKGROUND OF THE INVENTION

The kidneys are organs that perform several functions as one of the important eliminatory organs. They work not only as eliminatory organs that regulate the body's fluid volume, excrete wastes and adjust electrolyte content, but as endocrine organs that secrete hormones such as erythropoietin (for red blood cell production) and rennin (for blood pressure control) and control the metabolism of vitamin D3 to maintain parathyroid function and calcium metabolism. They also work as organs for metabolism that destroy a peptide hormone, reabsorb low molecular proteins, and regulate the glucose/lipid metabolism. The examples of kidney disease are nephritis, renal failure, kidney cancer, etc., and nephritis is the most typical kidney disease. In patients with continued nephritis, chronic renal failure, hypertension, or other diseases appear due to a loss of kidney function, causing complications such as damage to other organs, metabolic abnormality, or the like. The loss of kidney function goes unnoticed until 70% or more of the kidney function is gone. If renal failure remains unnoticed without an appropriate treatment, dialysis or kidney transplant is the only treatment for the patient. In South Korea, the number of patients going on dialysis is increasing by 4,000 to 5,000 each year, and the number of kidney transplant patients is also ascending. Continuous dialysis is necessary until kidney transplantation is done, resulting in a great pain or economic burden to the patient. As for kidney transplant, a lack of kidney donors causes a long wait, even with a social problem related to organ trafficking.

In case of immune-complex mediated nephritis that is found in about 70% of the patients with nephritis, antigens within/from the body bind to antibodies produced in the body to form antigen-antibody complexes, which deposit within glomerular basement membranes and mesangial cells to cause inflammation and damage on the glomeruli. Anti-glomerular basement membrane antibody nephritis induced by similar immune response is a disease that anti-glomerular basement membrane antibodies formed within the body deposit in the glomerular basement membranes to cause acute inflammation, and found in about 5% of the patients with nephritis. Contamination of urinary organs such as urinary tract, bladder, etc. with pathogenic bacteria or viruses may allow an ingress of pathogens into kidneys to induce nephritis.

The medications for nephritis include immune-suppressant drugs, anti-inflammatory drugs, hypertension/vasoactive drugs, antibiotics, and so forth. The immune-suppressant drugs reduce formation of antibodies, which triggers nephritis, to inhibit deposition of antigen-antibody complexes and anti-inflammatory drugs suppress inflammation, thereby improving nephritis symptoms. Angiotensin II antagonists used as hypertension/vasoactive drugs accelerate production of basement membranes that are vascular cell walls acting like glomerular filters, to activate the kidney functions. For infection-induced nephritis, quinolone antibiotics are used to kill pathogenic bacteria causing nephritis.

Patients with nephritis are mostly with autoimmune glomerulonephritis, which is treated primarily with immune-suppressant drugs, anti-inflammatory drugs, and hypertension/vasoactive drugs. Infection-induced pyelonephritis is treated with quinolone antibiotics. The examples of the immune-suppressant drugs for nephritis include tacrolimus, eculizumab, mycophenolate mofetil, cyclosporine A, etc. The examples of the anti-inflammatory drugs include dexamethasone, prednisolone, etc. The hypertension/vasoactive drugs for glomerulonephritis are, for example, candesartan, and rituximab and abatacept which have the antitumor activity. The medicines for pyelonephritis are levofloxacine and gatifloxacin. The patients with nephritis in other countries than Korea are mostly treated with immune-suppressant drugs, such as tacrolimus, mycophenolate mofetil, or eculizumab. In Korea, antibiotics are most commonly used medications for nephritis, and the use of immune-suppressant drugs for nephritis is increasing in recent years.

The long-term use of immune-suppressant drugs or antibiotics, however, results in adverse effects, including ulceration, edema, an increase of infection, hypertension, hepatotoxemia, and so forth, so immune-suppressant drugs and antibiotics are limited in use. Hence there is a demand for developing novel medicines for nephritis with less adverse effects than the existing medicines for nephritis and with secured safety.

For that reason, novel medicines for nephritis using natural substances have recently been developed.

DETAILED DESCRIPTION OF THE INVENTION

Summary or Invention

In an attempt to develop a composition for prevention and treatment of nephritis, the inventors of the present invention have found out that at least one herbal extract selected from the group consisting of a Crataegi Fructus extract, a Cinnamomi Cortex extract, a Prunella Spica extract, and an Equiseti Herba extract has preventive and therapeutic effects on nephritis, completing the present invention.

An embodiment of the present invention provides a composition for prevention and/or treatment of nephritis that contains at least one herbal extract selected from the group consisting of a Crataegi Fructus extract, a Cinnamomi Cortex extract, a Prunella Spica extract, and an Equiseti Herba extract, as an active ingredient.

Another embodiment provides a method for prevention and/or treatment of nephritis that comprises administrating a therapeutically effective amount of at least one herbal extract selected from the group consisting of a Crataegi Fructus extract, a Cinnamomi Cortex extract, a Prunella Spica extract, and an Equiseti Herba extract to a patient in need of prevention and/or treatment of nephritis.

Still another embodiment provides a use of at least one herbal extract selected from the group consisting of a Crataegi Fructus extract, a Cinnamomi Cortex extract, a Prunella Spica extract, and an Equiseti Herba extract for prevention and/or treatment of nephritis.

Technical Solution

The inventors of the present invention have found out that at least one herbal extract selected from the group consisting of a Crataegi Fructus extract, a Cinnamomi Cortex extract, a Prunella Spica extract, and an Equiseti Herba extract possesses a good therapeutic effect on a gentamicin- or cisplatin-induced nephritis model and an inhibitory effect on the growth of mesangial cells of the kidney, thus completing the present invention.

Accordingly, the present invention is characterized by the use of a composition for prevention and treatment of nephritis, wherein the composition contains at least one herbal extract selected from the group consisting of a Crataegi Fructus extract, a Cinnamomi Cortex extract, a Prunella Spica extract, and an Equiseti Herba extract, as a therapeutically effective ingredient.

Hereinafter, the present invention will be described in further detail as follows.

In accordance with an embodiment of the present invention, there is provided a composition for prevention and/or treatment of nephritis that contains a therapeutically effective amount of at least one herbal extract selected from the group consisting of a Crataegi Fructus extract, a Cinnamomi Cortex extract, a Prunella Spica extract, and an Equiseti Herba extract. In another embodiment of the present invention, there is provided a method for prevention and/or treatment of nephritis that comprises administrating a therapeutically effective amount of at least one herbal extract selected from the group consisting of a Crataegi Fructus extract, a Cinnamomi Cortex extract, a Prunella Spica extract, and an Equiseti Herba extract to a patient in need of prevention and/or treatment of nephritis. In still another embodiment of the present invention, there is provided a use of at least one herbal extract selected from the group consisting of a Crataegi Fructus extract, a Cinnamomi Cortex extract, a Prunella Spica extract, and an Equiseti Herba extract for prevention and/or treatment of nephritis, or in preparation of a composition for prevention and/or treatment of nephritis.

Crataegi Fructus is the fruit of *Crataegus pinnatifida* and its congeners in the rose family, Rosaceae and usually called "Hawthorn" in English. Found in highlands, the tree with gray bark and thorny branches can reach a height of 3 to 6 m. The leaves, arranged in an alternate pattern on the stem, are nearly egg-shaped, and 6 to 8 cm long and 5 to 6 cm wide. The leaf margin is divided into lobes like a feather, more deeply divided on the base. The leaf bears hairs on the midrib on both sides with an irregularly toothed margin. The leafstalk is 2 to 6 cm long. Crataegi Fructus is known to have pharmaceutical effects, such as of vasodilation, lowering blood pressure, antimicrobial action, antioxidation, and so forth.

Cinnamomi Cortex is the trunk bark of *Cinnamomum cassia* and its congeners in the Lauraceae family. The tree, as a leafy ornamental tree, can reach a height of at least 8 m with green branches. The flower, light green, has a clayx shortly divided into six sepals, which are arranged in two rows. This herb has been known to have therapeutic effects, such as of vasodilation, accelerating blood circulation, stimulating gastric activity, irritation relief, antioxidation, and so forth. As an herbal medicine, it has been used for treatment of headache, fever, nervous palpitation, severe pain, cold, or the like. Korean Patent Open-Laid Application No. 2006-0030535 (filed on Apr. 11, 2006) discloses a Cinnamomi Cortex extract having an anti-anxiety activity and a composition containing the same, where the Cinnamomi Cortex extract is reportedly used as a medical product or a health functional food for prevention and treatment of anxiety induced by disorders of the cranial nerve system.

Prunella Spica is a perennial herb of *Prunella vulgaris* and its congeners in the Labiatae family. This herb, all covered with white hairs, has a height of 20 to 30 cm with a square stem. After blossom drop, it begins to put forth its branches with leaves growing straight to about 2 to 5 cm in length. The leaf margin is smooth or a little bit toothed. In summer, the half-withered herbs are cut off and dried out in the sun into a nontoxic herbal medicine. This herb has been known to have therapeutic effects, such as of diuretic action, antimicrobial action, lowering blood pressure, antitumor action, antioxidation, and so forth. As an herbal medicine, it has been used for treatment of chronic abscess, scall, acute mastitis, tuberculous lymphadenitis, and so forth. It has also been used to destroy lumps induced by retention of fluid or blood clot in the lower abdomen, remedy beriberi, and treat numbness and tingling.

Equiseti Herba is a perennial herb of *Equisetum hiemale* and its congeners in the Equisetaceae family. This herb can reach a height of more than 20 cm with a short ground-creeping root stalk. The root node sends out a long dark brown root. The stem is rigid and round, about 4 to 8 cm in diameter, has 10 to 20 lines between nodes, and stands upright without branches. This herb has a color of grey green or yellow green on the outer surface and 8 to 30 vertical grooves, and is light-weighed with soft texture. It is known to have therapeutic effects, such as of diuretic action, antioxidation, and so forth. As an herbal medicine, it has been used for treatment of headache, fever, intestinal bleeding, or other bleedings.

However, the preventive and/or therapeutic effects of each herbal extract of Crataegi Fructus, Cinnamomi Cortex, Prunella Spica, and Equiseti Herba on nephritis have not been yet figured out and the studies regarding it remain to be desired.

The term "extract" as used herein inclusively refers to an extract of at least one selected from the group consisting Crataegi Fructus, Cinnamomi Cortex, Prunella Spica, and Equiseti Herba, and a concentrate and/or dried product obtained by concentrating and/or drying the extract through a conventional method. The extract, when it is of at least two herbs selected from the group consisting of Crataegi Fructus, Cinnamomi Cortex, Prunella Spica, and Equiseti Herba, may be "a mixture of herbal extracts" obtained by extracting at least two of the herbs with solvents, same as or different from each other, and mixing the extracts together; or "an extract of herbal mixture" obtained by mixing at least two of the herbs and extracting the herbal mixture. As can be seen from the following Experimental Example 1, both the mixture of herbal extracts and the extract of herbal mixture exhibit a good preventive and/or therapeutic effect on nephritis without any significant difference and thus can be included in the scope of the present invention.

The extract as defined in the present invention is preferably obtained by extraction with water, a linear or branched C1-C6 alcohol, or an aqueous solution of linear or branched C1-C6 alcohol. The solvent for extraction may be a 10 to 90% (v/v), preferably 10 to 70% (v/v), more preferably 50 to 70% (v/v) aqueous solution of linear or branched C1-C6 alcohol. More specifically, the solvent for extraction may be a 10 to 90% (v/v), preferably 10 to 70% (v/v), more preferably 50 to 70% (v/v) aqueous solution of ethanol.

Hereinafter, a detailed description will be given as to a method of preparing an extract of the present invention.

Each extract of Crataegi Fructus, Cinnamomi Cortex, Prunella Spica and Equiseti Herba according to the present invention can be obtained by chopping each dry herb; extracting the herb pieces with water, a linear or branched C1-C6 alcohol, or an aqueous alcohol solution (e.g., 10 to 90% (v/v), preferably 10 to 70% (v/v), more preferably 50 to 70% (v/v) aqueous solution of a linear or branched C1-C6 alcohol; preferably, 10 to 90% (v/v), preferably 10 to 70% (v/v), more preferably 50 to 70% (v/v) aqueous solution of ethanol) in an amount about 3 to 20 times, preferably about 5 to 15 times the weight (g) of the dry herb by percolation, hot water extraction, ultrasonic extraction, or reflux condensing extraction at 40 to 110° C., preferably 55 to 90° C. for about 0.5 to 20 hours, preferably 1 to 10 hours; and subjecting the obtained extract to filtration, concentration under reduced pressure and/or drying.

Using the solvent for extraction in an amount less than 3 times the weight of the dry herb results in difficulty of agitation to lower the solubility of the extract and deteriorate the extraction efficiency, while using the solvent in an amount more than 20 times the weight of the dry herb causes a need for a greater amount of the lower alcohol in the subsequent purification step, bringing about economic and handling problems. When using an alcohol solution as a solvent for extraction, an alcohol content of less than 10% (v/v) may result in an excess of polar substances such as sugar extracted from the herb, causing a problem in the subsequent filtration step, while an alcohol content exceeding 90% (v/v) may relatively increase the non-polarity of the solvent to lower the extraction efficiency for a desired active substance. The extraction temperature below 40° C. lowers the extraction efficiency, and the extraction temperature above 110° C. raises the extraction cost uneconomically due to the limited extraction efficiency. The extraction time less than 30 minutes lowers the extraction efficiency, and the extraction time longer than 20 hours brings about an unwanted extraction of impurities to lower the purity of the final extract.

After filtration of the extract, the filtrate is collected, and the residual is immersed in water, a linear or branched C1-C6 alcohol, or an aqueous alcohol solution (e.g., 10 to 90% (v/v), preferably 10 to 70% (v/v), more preferably 50 to 70% (v/v) aqueous solution of a linear or branched C1-C6 alcohol; preferably, 10 to 90% (v/v), preferably 10 to 70% (v/v), more preferably 50 to 70% (v/v) aqueous solution of ethanol), in an amount about 4 to 7 times the weight of the herb. The resultant solution is heated (e.g., at 55 to 90° C.) and subjected to a re-extraction (second extraction) for 2 to 5 hours. After a second filtration, the filtrate is collected and mixed with the previous filtrate to enhance the extraction efficiency. One embodiment of the present invention involves sequentially conducting a first extraction and then a second extraction. The second extraction is to avoid a deterioration of the extract efficiency that possibly occurs due to the high water content of the herb and a consequent loss even after an efficient filtration when the first extraction is conducted solely in the large-scaled production of an herbal extract. But the second extraction is carried out only for the extraction efficiency and has nothing to do with the therapeutic effect of the final extract. It is therefore understood that the herbal extracts as an active ingredient of the present invention are not limited by the above-described preparation method.

An evaluation of the step-based extraction efficiencies reveals that about 80 to 90% of the extract in total amount is acquired in the second extraction and that a third extraction can be conducted but is not so beneficial in the economic aspect. The mixed filtrate after the second extraction is concentrated under pressure at 50 to 60° C. to eliminate the solvent remaining in the sample. The sample concentrate after complete concentration under reduced pressure undergoes two or three azeotropic concentrations with water, which is 25 to 50 times the total weight of the concentrate, and mixed with a same amount of more water to form a homogeneous suspension. The suspension is then lyophilized into the final extract. The use of water for azeotropic concentrations is to effectively control the content of the lower alcohol remaining in the herbal extract for the purpose of using the herbal extract as a material for medicinal products.

In accordance with a preferred embodiment of the present invention, the herbal extract comprises a composition containing a Crataegi Fructus extract and a Cinnamomi Cortex extract mixed at a weight ratio (i.e., the weight of the Crataegi Fructus extract:the weight of the Cinnamomi Cortex extract) of 10:1 to 1:5, preferably 5:1 to 1:5, more preferably 1:1 to 1:5.

In accordance with another preferred embodiment of the present invention, the herbal extract comprises a composition containing a Crataegi Fructus extract and a Prunella Spica extract mixed at a weight ratio (i.e., the weight of the Crataegi Fructus extract:the weight of the Prunella Spica extract) of 10:1 to 1:5.

In accordance with further another preferred embodiment of the present invention, the herbal extract comprises a composition containing a Crataegi Fructus extract and an Equiseti Herba extract mixed at a weight ratio (i.e., the weight of the Crataegi Fructus extract:the weight of the Equiseti Herba extract) of 10:1 to 1:5.

In accordance with further another preferred embodiment of the present invention, the herbal extract comprises a composition containing a Cinnamomi Cortex extract and a Prunella Spica extract mixed at a weight ratio (i.e., the weight of the Cinnamomi Cortex extract:the weight of the Prunella Spica extract) of 10:1 to 1:5, preferably 1:1 to 1:3.

In accordance with further another preferred embodiment of the present invention, the herbal extract comprises a composition containing a Cinnamomi Cortex extract and an Equiseti Herba extract mixed at a weight ratio (i.e., the weight of the Cinnamomi Cortex extract:the weight of the Equiseti Herba extract) of 7:1 to 1:7.

In accordance with further another embodiment of the present invention, the herbal extract comprises a composition containing a Prunella Spica extract and an Equiseti Herba extract mixed at a weight ratio (i.e., the weight of the Prunella Spica extract:the weight of the Equiseti Herba extract) of 10:1 to 1:10.

In accordance with still further another preferred embodiment of the present invention, the herbal extract comprises a composition containing a Crataegi Fructus extract, a Cinnamomi Cortex extract, and a Prunella Spica extract mixed at a weight ratio (i.e., the weight of the Crataegi Fructus extract:the weight of the Cinnamomi Cortex extract:the weight of the Prunella Spica extract) of 10:1:1 to 1:1:5.

In accordance with still further another preferred embodiment of the present invention, the herbal extract comprises a composition containing a Crataegi Fructus extract, a Cinnamomi Cortex extract, and an Equiseti Herba extract mixed at a weight ratio (i.e., the weight of the Crataegi Fructus extract:the weight of the Cinnamomi Cortex extract:the weight of the Equiseti Herba extract) of 10:1:1 to 1:1:5.

In accordance with still further another preferred embodiment of the present invention, the herbal extract comprises a composition containing a Crataegi Fructus extract, a Prunella Spica extract, and an Equiseti Herba extract mixed at a weight ratio (i.e., the weight of the Crataegi Fructus extract:the weight of the Prunella Spica extract:the weight of the Equiseti Herba extract) of 7:1:1 to 1:1:5.

In accordance with still further another preferred embodiment of the present invention, the herbal extract comprises a composition containing a Cinnamomi Cortex extract, a Prunella Spica extract, and an Equiseti Herba extract mixed at a weight ratio (i.e., the weight of the Cinnamomi Cortex extract:the weight of the Prunella Spica extract:the weight of the Equiseti Herba extract) of 7:1:1 to 1:1:7.

In accordance with still further another preferred embodiment of the present invention, the herbal extract comprises a composition containing a Crataegi Fructus extract, a Cinnamomi Cortex extract, a Prunella Spica extract, and an Equiseti Herba extract mixed at a weight ratio (i.e., the weight of the Crataegi Fructus extract:the weight of the Cinnamomi Cortex extract:the weight of the Prunella Spica extract:the weight of the Equiseti Herba extract) of 5:1:1:1 to 1:1:1:5.

The weight ratio of the extracts is based on 'the dry weight of the extract', which means the weight of the dry extract obtained by removing the solvent from the extract (hereinafter, the rest is the same as above).

The term "nephritis" as defined herein may include at least one selected from the group consisting of glomerulonephritis, pyelonephritis, interstitial nephritis, lupus nephritis, diabetic nephropathy, proteinuria, tubular atrophy, glomerulosclerosis, renal failure, and so forth.

The composition for prevention and treatment of nephritis according to the present invention comprises, based on the total weight of the composition, 0.001 to 99 wt. %, preferably 0.1 to 50 wt. % of the extract. The content of the extract is not specifically limited to the above range and may be adequately controlled depending on the type and progress of a disease being treated, the patient's condition, a desired effect, and so forth.

The composition comprising the extract of the present invention may further comprise appropriate carriers, excipients, or diluents, generally used in preparation of a pharmaceutical composition.

The composition comprising the extract of the present invention may be, according to a traditional method, formulated into oral dosage forms (e.g., powder, granule, tablet, capsule, suspension, emulsion, syrup, aerosol, etc.), topical medication formulations, rectal formulations, or injectable formulations. The carriers, excipients or diluents that can be included in the composition comprising the extract may be lactose, dextrose, sucrose, sorbitol, mannitol, xylitol, erythritol, maltitol, starch, acasia rubber, alginate, gelatin, calcium phosphate, calcium silicate, cellulose, methyl cellulose, amorphous cellulose, polyvinyl pyrrolidone, water, methylhydroxybenzoate, propylhydroxybenzoate, talc, magnesium stearate, mineral oil, etc. The formulation of the composition may involve using general diluents or excipients such as fillers, bulking agents, binders, wetting agents, disintegrants, surfactants, etc. The solid formulations for oral administration may include tablets, pills, powders, granules, capsules, etc. The solid formulations may be prepared by mixing the extract with at least one excipient, such as, for example, starch, calcium carbonate, sucrose, lactose, gelatin, etc. In addition to such general excipients, lubricants such as magnesium stearate or talc may also be used. The liquid formulations for oral administration may include suspensions, solutions, oils, syrups, etc. In addition to general diluents such as water and liquid paraffin, different excipients may also be used, such as, for example, wetting agents, flavors, fragrances, preserves, etc. The formulations for parenteral administration may include sterile aqueous solutions, nonaqueous solvents, suspensions, oils, lyophilized preparations, or rectal preparations. The nonaqueous solutions and the suspensions may include propylene glycol, polyethylene glycol, vegetable oil (e.g., olive oil), injectable ester (e.g., ethyloleate), etc. The base for rectal formulations may include witepsol, macrogol, tween 61, cacao butter, laurin butter, glycerogelatin, etc.

To acquire desirable effects, for example, the composition may be administered at a daily dosage of, based on the dry weight of the extract, 1 to 1,000 mg/kg, preferably 50 to 500 mg/kg, more preferably 150 to 300 mg/kg. The administration may be conducted once or several times a day. But the daily dosage may be appropriately controlled by those skilled in the art depending on the patient's condition and weight, the severity of the disease, the dosage form, and the administration route and time. Hence, the daily dosage as specified above is not intended to limit the scope of the present invention in any aspects.

The composition of the present invention may be administered to all mammals, preferably rodents, domestic animals, humans, or the like, more preferably humans. The administration route may include all types of routes, including, but not specifically limited to, oral route, rectal route, or intravenous, intramuscular, subcutaneous, intrauterine epidural or intracerebrocentricular injection route.

In another embodiment, the present invention provides a health functional food for prevention and/or improvement of nephritis that contains, as an active ingredient, at least one herbal extract selected from the group consisting of a Crataegi Fructus extract, a Cinnamomi Cortex extract, a Prunella Spica extract, and an Equiseti Herba extract, The composition comprising the extract of the present invention may be used in a variety of applications, such as medicines or health functional foods for prevention and improvement of nephritis. The foods to which the extract of the present invention can be added may include, for example, any kind of foods, beverages, gums, teas, vitamin complexes, health functional foods, and may be used in the form of powders, granules, tablets, capsules, or beverages.

The extract of the present invention nearly has neither toxicity nor side effects and may be used as a safe medicinal substance for long-term administration for preventive purpose.

The content of the extract in the health functional food may be in the range of 0.01 to 15 wt. % based on the total weight of the food as a composition for health functional food of the present invention; or 0.02 to 10 g, preferably 0.3 to 1 g based on 100 ml of the food as a composition for health functional beverage.

The composition for health functional beverage among the health functional foods may comprise, as essential ingredients, the extract and a liquid ingredient, which is not specifically limited and may additionally include various flavors or natural hydrocarbons as in a traditional beverage. The examples of the natural carbohydrates may include general sugars such as monosaccharides (e.g., glucose, fructose, etc.), disaccharides (e.g., maltose, sucrose, etc.), or polysaccharides (e.g., dextrin, cyclodextrin, etc.); or sugar alcohols such as xylitol, sorbitol, erythritol, etc. The flavors as used herein may preferably include natural flavors (e.g., thaumatin, Stevia extract, rebaudioxide A, glycyrrhizin, etc.), or synthetic flavors (e.g., saccharine, aspartame, etc.). The natural carbohydrate may be used in an amount of about 1 to 20 g, preferably about 5 to 12 g per 100 ml of the composition of the present invention.

In addition to the above ingredients, the composition of the present invention may further include various nutritional supplements, vitamins, minerals (electrolytes), flavors (e.g., synthetic flavors, natural flavors, etc.), colors, fillers (e.g., cheese, chocolate, etc.) pectic acid and its salts, alginic acid and its salts, organic acids, protective colloid thickening agent, pH regulator, stabilizer, preservative, glycerin, alcohol, carbonating agent used for carbonated drink, and so forth. The compositions of the present invention may further include natural fruit juice, and fruit pulp for preparation of fruit juice or vegetable juice. These ingredients may be used alone or in combination. The content of the additives is not so significant but may be selected within the range of 0 to 20 parts by weight per 100 parts by weight of the composition of the present invention.

In another embodiment of the present invention, there is provided a method for preparing a composition for prevention and/or treatment of nephritis that comprises:

conducting a first extraction for extracting at least one herb selected from the group consisting of Crataegi Fructus, Cinnamomi Cortex, Prunella Spica and Equiseti Herba with water, a linear or branched C1-C6 alcohol, or an aqueous alcohol solution (e.g., a 10 to 90% (v/v), preferably 10 to 70% (v/v), more preferably 50 to 70% (v/v) aqueous solution of a linear or branched C1-C6 alcohol; preferably, a 10 to 90% (v/v), preferably 10 to 70% (v/v), more preferably 50 to 70% (v/v) aqueous solution of ethanol) in an amount about 3 to 20 times, preferably about 5 to 15 times the weight (g) of the herb by percolation, hot water extraction, ultrasonic extraction, or reflux condensing extraction at an extraction temperature of 40 to 110° C., preferably 55 to 90° C. for about 0.5 to 20 hours, preferably about 1 to 10 hours to yield an herbal extract.

In one preferred embodiment of the present invention, the method may further comprise, after the first extraction:

filtering the extract from the first extraction to collect a filtrate;

conducting a second extraction for extracting a residue other than the filtrate with water, a linear or branched C1-C6 alcohol, or an aqueous alcohol solution (e.g., a 10 to 90% (v/v), preferably 10 to 70% (v/v), more preferably 50 to 70% (v/v) aqueous solution of a linear or branched C1-C6 alcohol; preferably, a 10 to 90% (v/v), preferably 10 to 70% (v/v), more preferably 50 to 70% (v/v) aqueous solution of ethanol) in an amount 4 to 7 times the weight of the residue at a raised temperature (e.g., 55 to 99° C.) for 2 to 5 hours; and filtering the extract from the second extraction and mixing the resultant filtrate with the filtrate of the first extraction.

Conducting both the first and second extractions enhances the extraction efficiency, which is beneficial to a large-scaled production of the herbal extract.

When the extract is from at least two herbs selected from the group consisting of Crataegi Fructus, Cinnamomi Cortex, Prunella Spica and Equiseti Herba, the extract may be prepared by obtaining individual extracts of the herbs and then mixing the extracts; or mixing the at least two herbs and then preparing an extract of the mixture according to the above-specified method. The mixing ratio of the individual herbal extracts is as defined above.

BEST MODE FOR CARRYING OUT THE INVENTION

The present invention will be hereafter described in detail with reference to the following examples, which are only for illustrative purposes and are not intended to limit the scope of the present invention.

Example 1

Preparation (A) of Single Herb Extracts 1.1: Preparation of Crataegi Fructus Extract Leaves and flowers of Crataegi Fructus (purchase from Kyung-dong market in South Korea) were washed with water to remove impurities and thoroughly dried. 2.0 L of a 60% (v/v) aqueous ethanol solution was added to 250 g of the dried leaves and flowers of Crataegi Fructus. After 3-hour reflux at 80° C. twice, the resultant liquid extract was filtered and concentrated under reduced pressure. Once most of water was vaporized, 0.2 L of water was added to the concentrated extract, which was then heated for azeotropic concentration. This procedure was repeated twice more. A same volume of water was added to the azeotropic concentrate to form a homogeneous suspension, which was then lyophilized to yield 45.0 g (18.0% yield with respect to the original herb) of a Crataegi Fructus extract in the powder form.

1.2: Preparation of Cinnamomi Cortex Extract

Cinnamomi Cortex (purchase from Kyung-dong market in South Korea) was washed with water to remove impurities and thoroughly dried. 2.0 L of a 60% (v/v) aqueous ethanol solution was added to 250 g of the dried Cinnamomi Cortex. After 3-hour reflux at 80° C. twice, the resultant liquid extract was filtered and concentrated under reduced pressure. Once most of water was vaporized, 0.2 L of water was added to the concentrated extract, which was then heated for azeotropic concentration. This procedure was repeated twice more. A same volume of water was added to the azeotropic concentrate to form a homogeneous suspension, which was then lyophilized to yield 28.5 g (11.4% yield with respect to the original herb) of a Cinnamomi Cortex extract in the powder form.

1.3: Preparation of Prunella Spica Extract

Prunella Spica was washed with water to remove impurities and thoroughly dried. 2.0 L of a 60% (v/v) aqueous ethanol solution was added to 250 g of the dried Prunella Spica. After 3-hour reflux at 80° C. twice, the resultant liquid extract was filtered and concentrated under reduced pressure. Once most of water was vaporized, 0.2 L of water was added to the concentrated extract, which was then heated for azeotropic concentration. This procedure was repeated twice more. A same volume of water was added to the azeotropic concentrate to form a homogeneous suspension, which was then lyophilized to yield 27.3 g (10.9% yield with respect to the original herb) of a Prunella Spica extract in the powder form.

1.4 Preparation of Equiseti Herba Extract

Equiseti Herba was washed with water to remove impurities and thoroughly dried. 2.0 L of a 60% (v/v) aqueous ethanol solution was added to 250 g of the dried Equiseti Herba. After 3-hour reflux at 80° C. twice, the resultant liquid extract was filtered and concentrated under reduced pressure. Once most of water was vaporized, 0.2 L of water was added to the concentrated extract, which was then heated for azeotropic concentration. This procedure was repeated twice more. A same volume of water was added to the azeotropic concentrate to form a homogeneous suspension, which was then lyophilized to yield 52.0 g (20.8% yield with respect to the original herb) of an Equiseti Herba extract in the powder form.

Example 2

Preparation of Extract of Herbal Mixture

Crataegi Fructus, Cinnamomi Cortex, and Prunella Spica were washed with water to remove impurities and thoroughly dried. 2.0 L of a 60% (v/v) aqueous ethanol solution was added to a mixture of the dried herbs, Crataegi Fructus (97 g) and Cinnamomi Cortex (153 g); or a mixture of the dried herbs, Cinnamomi Cortex (92 g) and Prunella Spica (96 g). After 3-hour reflux at 80° C. twice, the resultant liquid extract was filtered and concentrated under reduced pressure. Once most of water was vaporized, 0.2 L of water was added to the concentrated extract, which was then heated for azeotropic concentration. This procedure was repeated twice more. A same volume of water was added to the azeotropic concentrate to form a homogeneous suspension, which was then lyophilized to yield 35.2 g (14.1% yield with respect to the original herbs) of a composite extract of Crataegi Fructus and Cinnamomi Cortex, and 22.0 g (11.7% yield with respect to the original herbs) of a composite extract of Cinnamomi Cortex and Prunella Spica in the powder form.

Example 3

Preparation of Mixture of Herbal Extracts

Example 3.1

Preparation of Mixture of Crataegi Fructus Extract and Cinnamomi Cortex Extract The Crataegi Fructus extract of Example 1.1 and the Cinnamomi Cortex extract of Example 1.2 were mixed together at weight ratios of 10:1, 5:1, 3:1, 1:1, 1:3, and 1:5 (the weight of the Crataegi Fructus extract:the weight of the Cinnamomi Cortex extract). For homogeneous mixing, to each mixture of the herbal extracts was added water in a volume 2 to 3 times the weight of the mixture, and the mixture was concentrated under reduced pressure at 50 to 60° C. A same volume of water was added to the resultant concentrate to form a homogeneous suspension, which was then lyophilized to yield a powder mixture.

Example 3.2

Preparation of Mixture of Crataegi Fructus Extract and Prunella Spica Extract The Crataegi Fructus extract of Example 1.1 and the Prunella Spica extract of Example 1.3 were mixed together at weight ratios of 10:1, 5:1, 3:1, 1:1, 1:3, and 1:5 (the weight of the Crataegi Fructus extract:the weight of the Prunella Spica extract). The procedures were conducted in the same manner of Example 3.1 to prepare a mixture.

Example 3.3

Preparation of Mixture of Crataegi Fructus Extract and Equiseti Herba Extract The Crataegi Fructus extract of Example 1.1 and the Equiseti Herba extract of Example 1.4 were mixed together at weight ratios of 10:1, 5:1, 3:1, 1:1, 1:3, and 1:5 (the weight of the Crataegi Fructus extract:the weight of the Equiseti Herba extract). The procedures were conducted in the same manner of Example 3.1 to prepare a mixture.

Example 3.4

Preparation of Mixture of Cinnamomi Cortex Extract and Prunella Spica Extract The Cinnamomi Cortex extract of Example 1.2 and the Prunella Spica extract of Example 1.3 were mixed together at weight ratios of 10:1, 5:1, 4:1, 3:1, 1:1, 1:3, and 1:5 (the weight of the Cinnamomi Cortex extract:the weight of the Prunella Spica extract). The procedures were conducted in the same manner of Example 3.1 to prepare a mixture.

Example 3.5

Preparation of Mixture of Cinnamomi Cortex Extract and Equiseti Herba Extract The Cinnamomi Cortex extract of Example 1.2 and the Equiseti Herba extract of Example 1.4 were mixed together at weight ratios of 7:1, 5:1, 3:1, 2:1, 1:1, 1:3, 1:5, and 1:7 (the weight of the Cinnamomi Cortex extract:the weight of the Equiseti Herba extract). The procedures were conducted in the same manner of Example 3.1 to prepare a mixture.

Example 3.6

Preparation of Mixture of Prunella Spica Extract and Equiseti Herba Extract The Prunella Spica extract of Example 1.3 and the Equiseti Herba extract of Example 1.4 were mixed together at weight ratios of 10:1, 5:1, 3:1, 1:1, 1:3, 1:5, and 1:10 (the weight of the Prunella Spica extract:the weight of the Equiseti Herba extract). The procedures were conducted in the same manner of Example 3.1 to prepare a mixture.

Example 3.7

Preparation of Mixture of Crataegi Fructus Extract, Cinnamomi Cortex Extract, and Prunella Spica Extract The Crataegi Fructus extract of Example 1.1, the Cinnamomi Cortex extract of Example 1.2, and the Prunella Spica extract of Example 1.3 were mixed together at weight ratios of 10:1:1, 2:2:3, and 1:1:5 (the weight of the Crataegi Fructus extract:the weight of the Cinnamomi Cortex extract:the weight of the Prunella Spica extract). The procedures were conducted in the same manner of Example 3.1 to prepare a mixture.

Example 3.8

Preparation of Mixture of Crataegi Fructus Extract, Cinnamomi Cortex Extract, and Equiseti Herba Extract The Crataegi Fructus extract of Example 1.1, the Cinnamomi Cortex extract of Example 1.2, and the Equiseti Herba extract of Example 1.4 were mixed together at weight ratios of 10:1:1, 2:5:2, and 1:1:5 (the weight of the Crataegi Fructus extract:the weight of the Cinnamomi Cortex extract:the weight of the Equiseti Herba extract). The procedures were conducted in the same manner of Example 3.1 to prepare a mixture.

Example 3.9

Preparation of Mixture of Crataegi Fructus Extract, Prunella Spica Extract, and Equiseti Herba Extract The Crataegi Fructus extract of Example 1.1, the Prunella Spica extract of Example 1.3, and the Equiseti Herba extract of Example 1.4 were mixed together at weight ratios of 7:1:1, 3:2:4, and 1:1:5 (the weight of the Crataegi Fructus extract: the weight of the Prunella Spica extract:the weight of the Equiseti Herba extract). The procedures were conducted in the same manner of Example 3.1 to prepare a mixture.

Example 3.10

Preparation of Mixture of Cinnamomi Cortex Extract, Prunella Spica Extract, and Equiseti Herba Extract The Cinnamomi Cortex extract of Example 1.2, the Prunella Spica extract of Example 1.3, and the Equiseti Herba extract of Example 1.4 were mixed together at weight ratios of 7:1:1, 3:2:5, and 1:1:7 (the weight of the Cinnamomi Cortex extract:the weight of the Prunella Spica extract:the weight of the Equiseti Herba extract). The procedures were conducted in the same manner of Example 3.1 to prepare a mixture.

Example 3.11

Preparation of Mixture of Crataegi Fructus Extract, Cinnamomi Cortex extract, Prunella Spica extract, and Equiseti Herba Extract The Crataegi Fructus extract of Example 1.1, the Cinnamomi Cortex extract of Example 1.2, the Prunella Spica extract of Example 1.3, and the Equiseti Herba extract of Example 1.4 were mixed together at weight ratios of 5:1:1:1, 3:2:2:2, and 1:1:1:5 (the weight of the Crataegi Fructus extract:the weight of the Cinnamomi Cortex extract:the weight of the Prunella Spica extract:the weight of the Equiseti Herba extract). The procedures were conducted in the same manner of Example 3.1 to prepare a mixture.

EXPERIMENTAL EXAMPLES

Evaluation of Pharmacological Activity

Experimental Example 1

Comparison in Activity Between Mixture of Herbal Extracts and Extract of Herbal Mixture Tests were conducted according to an evaluation method (Amin et al., *Environmental Health Perspectives* vol. 112, No. 4, March, 2004, 465-479) to compare and evaluate the therapeutic effects on nephritis of the extracts from a herbal mixture of Crataegi Fructus and Cinnamomi Cortex and a herbal mixture of Cinnamomi Cortex and Prunella Spica in Example 2, and a 1:1 mixture of the Crataegi Fructus extract and the Cinnamomi Cortex extract in Example 3.1 and a 1:1 mixture of the Cinnamomi Cortex extract and the Prunella Spica extract in Example 3.4. The results are presented in Table 1.

A normal group was subjected to the tests, where a nephritis-inducing factor, gentamicin (purchased from Whail Pharma. Co., Ltd.) was administered to male SD rats (7 weeks old, 195-205 g, Orient) at a dosage of 240 mg/kg for 6 days through an intraperitioneal injection to induce nephritis. Among the test rats with induced nephritis, the test groups other than the negative control group received the 2 test drugs of Example 2 or the test drug of Example 3.1 or 3.4 orally at a daily dosage of 400 mg/kg. The test rats were autopsied 7 days after the oral administrations. The blood samples collected were analyzed to detect blood urea nitrogen (B.U.N.) and creatinine. The results are presented in Table 1.

TABLE 1

| Group | Dosage (mg/kg) | B.U.N. (mg/dl) | Creatinine (mg/dl) |
|---|---|---|---|
| Mixture of *Crataegi Fructus* extract and *Cinnamomi Cortex* extract (Example 3.1) | 400 | 21.30 | 0.73 |
| Extract of Herbal Mixture of *Crataegi Fructus* and *Cinnamomi Cortex* (Example 2) | 400 | 21.48 | 0.74 |
| Mixture of *Cinnamomi Cortex* extract and *Prunella Spica* extract (Example 3.4) | 400 | 20.81 | 0.68 |
| Extract of Herbal Mixture of *Cinnamomi Cortex* and *Prunella Spica* (Example 2) | 400 | 20.89 | 0.69 |
| Negative Control Group | — | 91.16 | 1.80 |
| Normal Group | — | 20.41 | 0.66 |

As can be seen from Table 1, the mixture of herbal extracts in Example 3.1 or 3.4 and the extracts of herbal mixtures in Example 2 were all excellent in therapeutic effect for nephritis. Particularly, there was no significant difference in activity depending on the preparation method.

Experimental Example 2

Test of Therapeutic Effect on Gentamicin-Induced Nephritis Model

Evaluation tests were conducted according to an evaluation method (Amin et al., *Environmental Health Perspectives* vol. 112, No. 4, March, 2004, 465-479) to investigate the therapeutic effect for nephritis of the single herb extracts of Example 1 and the mixtures of herbal extracts in Examples 3.1 to 3.11. The evaluation results for the single herb extracts of Example 1 are presented in Table 1, and the results for the mixtures of herbal extracts are in Table 2.

A normal group other than a positive control group was subjected to the tests, where a nephritis-inducing factor, gentamicin (purchased from Whail Pharma. Co., Ltd.) was administered intraperitioneally to male SD rats (7 weeks old, 195-205 g, Orient) at an injection dosage of 240 mg/kg to induce nephritis. Among the test rats with induced nephritis, the test group other than the negative control group received the 4 test drugs of Example 1 and the 11 test drugs of Examples 3 orally at a daily dosage of 400 mg/kg. The test rats were autopsied 7 days after the oral administrations. The blood samples collected were analyzed to measure the levels of blood urea nitrogen (B.U.N.) and creatinine.

TABLE 2

| Group | | Dosage (mg/kg) | B.U.N. (mg/dl) | Creatinine (mg/dl) |
|---|---|---|---|---|
| Example 1.1 | | 400 | 30.55 | 0.78 |
| Example 1.2 | | 400 | 23.05 | 0.75 |
| Example 1.3 | | 400 | 45.06 | 0.98 |
| Example 1.4 | | 400 | 37.57 | 0.82 |
| Example 3.1 (Crataegi Fructus:Cinnamomi Cortex) | 10:1 | 400 | 25.11 | 0.77 |
| | 5:1 | 400 | 21.43 | 0.73 |
| | 3:1 | 400 | 21.13 | 0.72 |
| | 1:1 | 400 | 20.81 | 0.68 |
| | 1:3 | 400 | 20.87 | 0.69 |
| | 1:5 | 400 | 20.51 | 0.68 |
| Example 3.2 (Crataegi Fructus:Prunella Spica) | 10:1 | 400 | 31.94 | 0.80 |
| | 5:1 | 400 | 31.35 | 0.81 |
| | 3:1 | 400 | 31.17 | 0.80 |
| | 1:1 | 400 | 34.44 | 0.82 |
| | 1:3 | 400 | 36.61 | 0.82 |
| | 1:5 | 400 | 37.81 | 0.84 |
| Example 3.3 (Crataegi Fructus:Equiseti Herba) | 10:1 | 400 | 29.60 | 0.76 |
| | 5:1 | 400 | 30.63 | 0.78 |
| | 3:1 | 400 | 30.58 | 0.77 |
| | 1:1 | 400 | 31.13 | 0.79 |
| | 1:3 | 400 | 33.85 | 0.82 |
| | 1:5 | 400 | 33.90 | 0.82 |
| Example 3.4 (Cinnamomi Cortex:Prunella Spica) | 10:1 | 400 | 28.25 | 0.78 |
| | 5:1 | 400 | 21.80 | 0.70 |
| | 4:1 | 400 | 21.71 | 0.72 |
| | 3:1 | 400 | 21.55 | 0.69 |
| | 1:1 | 400 | 20.99 | 0.67 |
| | 1:3 | 400 | 21.02 | 0.68 |
| | 1:5 | 400 | 31.03 | 0.81 |
| Example 3.5 (Cinnamomi Cortex:Equiseti Herba) | 7:1 | 400 | 27.37 | 0.78 |
| | 5:1 | 400 | 26.77 | 0.77 |
| | 3:1 | 400 | 25.13 | 0.77 |
| | 2:1 | 400 | 24.74 | 0.75 |
| | 1:1 | 400 | 24.61 | 0.75 |
| | 1:3 | 400 | 28.11 | 0.79 |
| | 1:5 | 400 | 30.98 | 0.80 |
| | 1:7 | 400 | 31.09 | 0.80 |
| Example 3.6 (Prunella Spica:Equiseti Herba) | 10:1 | 400 | 40.46 | 0.89 |
| | 5:1 | 400 | 36.57 | 0.83 |
| | 3:1 | 400 | 35.93 | 0.82 |
| | 1:1 | 400 | 35.14 | 0.81 |
| | 1:3 | 400 | 36.14 | 0.83 |
| | 1:5 | 400 | 36.37 | 0.84 |
| | 1:10 | 400 | 36.10 | 0.82 |
| Example 3.7 (Crataegi Fructus:Cinnamomi Cortex:Prunella Spica) | 10:1:1 | 400 | 28.81 | 0.78 |
| | 2:2:3 | 400 | 22.34 | 0.74 |
| | 1:1:5 | 400 | 30.35 | 0.78 |
| Example 3.8 (Crataegi Fructus:Cinnamomi Cortex:Equiseti Herba) | 10:1:1 | 400 | 26.70 | 0.77 |
| | 2:5:2 | 400 | 20.07 | 0.68 |
| | 1:1:5 | 400 | 22.14 | 0.71 |
| Example 3.9 (Crataegi Fructus:Prunella Spica:Equiseti Herba) | 7:1:1 | 400 | 30.83 | 0.78 |
| | 3:2:4 | 400 | 31.41 | 0.82 |
| | 1:1:5 | 400 | 32.37 | 0.84 |
| Example 3.10 (Cinnamomi Cortex:Prunella Spica:Equiseti Herba) | 7:1:1 | 400 | 21.12 | 0.71 |
| | 3:2:5 | 400 | 28.78 | 0.76 |
| | 1:1:7 | 400 | 32.34 | 0.82 |
| Example 3.11 (Crataegi Fructus:Cinnamomi Cortex:Prunella Spica:Equiseti Herba) | 5:1:1:1 | 400 | 23.14 | 0.73 |
| | 3:2:2:2 | 400 | 21.11 | 0.71 |
| | 1:1:1:5 | 400 | 28.17 | 0.77 |
| Negative Control Group | | — | 89.20 | 1.79 |
| Normal Group | | — | 19.84 | 0.63 |

As can be seen from Table 2, as well as the single herb extracts of Examples 1.1 to 1.4, the mixtures of the herbal extracts of Examples 3.1 to 3.11 by the above-defined compositions were all excellent in therapeutic effect for nephritis. In particular, a composition having a good activity according to the mixing proportion of each ingredient was determined, and the composite drugs containing Crataegi Fructus or Cinnamomi Cortex showed an overall good activity on the gentamicin-induced nephritis model.

Experimental Example 3

Histopathological Investigation on Gentamicin-Induced Nephritis Model

From a test group treated with the 5:1 mixture of the Crataegi Fructus extract and the Cinnamomi Cortex extract in Example 3.1, a kidney tissue was harvested and subjected to histopathological investigation.

The kidney tissue harvested was formalin-fixed and cut into sections following a general tissue processing procedure. The kidney tissue sections were stained with hematoxylin and eosin (purchased from Sigma) and observed. Upon recognition of unusual histopathological findings, the severity of lesions was scored into four grades from minimal to marked severities.

Figure 1:
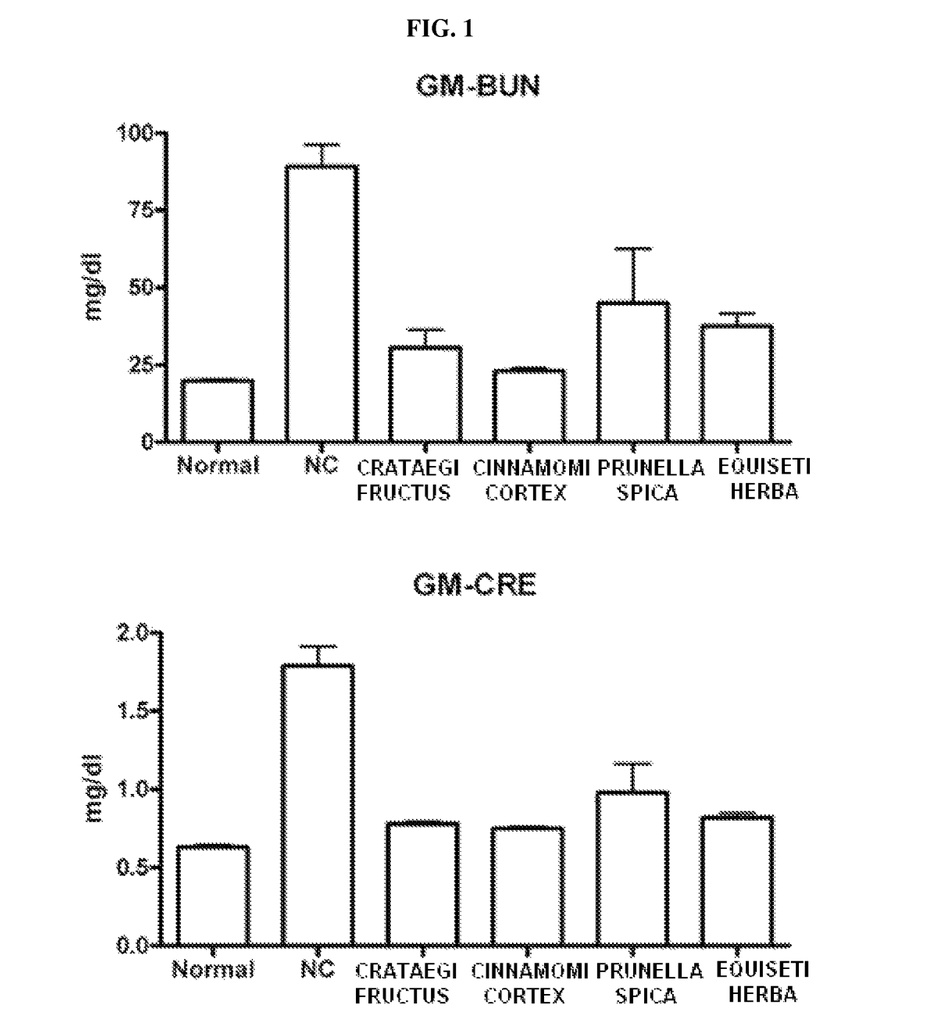
FIG. 1 shows the nephritis inhibitory activity of single herb extracts on a gentamicin-induced nephritis model.
Figure 2:
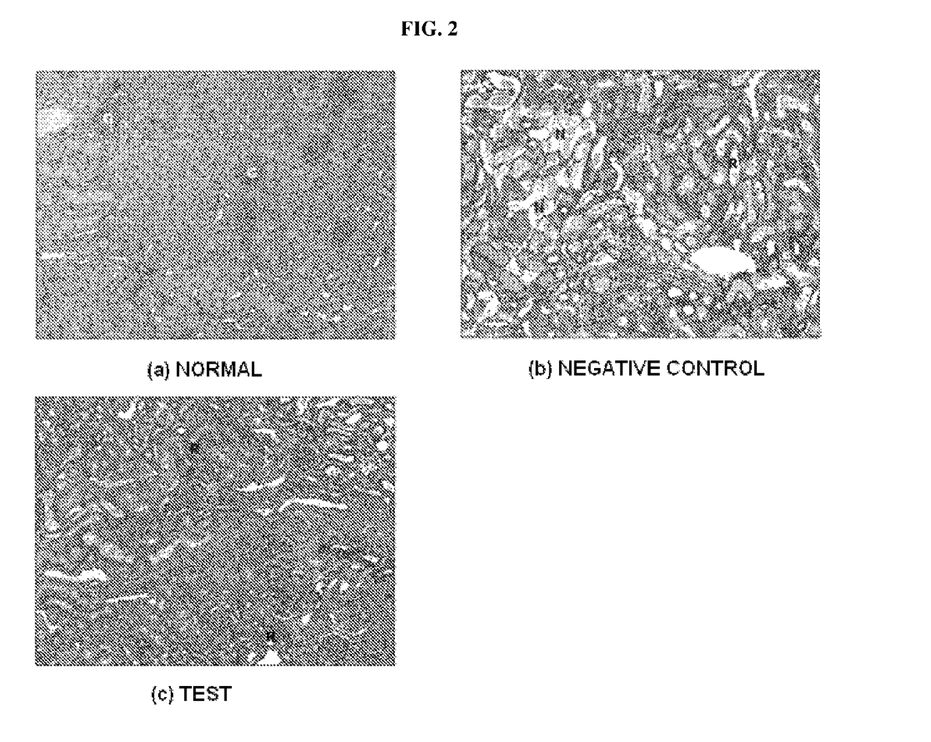
FIG. 2 shows the results of a histopathological investigation on the gentamicin-induced nephritis model.

The pathological changes of the kidney tissue are presented in FIG. 2. In the normal group of FIG. 2(a), where G is glomeruli and T is renal tubules, there was no noticeable lesion in regard to nephritis. In the negative control group of FIG. 2(b) (i.e., the test group with nephritis treated with no test drug), there were severe lesions, such as tubular necrosis 'N' (marked, grade 4+), tubular regeneration 'R' (moderate, grade 3+), and interstitial inflammation '*' (moderate, grade 3+). Other lesions recognized were hyaline casts "→" in a tubular lumen, tubular dilation, hyaline droplet, interstitial fibrosis, and so forth. The test group of FIG. 2(c) treated with the test drugs of Example 3.1 had lesions, such as tubular necrosis "N" (minimal, grade 1+), tubular regeneration "R" (moderate, grade 3+), and interstitial inflammation "*" (mild, grade 2+).

It can be seen from the results of FIG. 2 that relative to the negative control group, the test group had a remarkable improvement in therapeutic effect for nephritis according to the histopathological observation.

Experimental Example 4

Test of Therapeutic Effect on Cisplatin-Induced Nephritis Model

Figure 3:
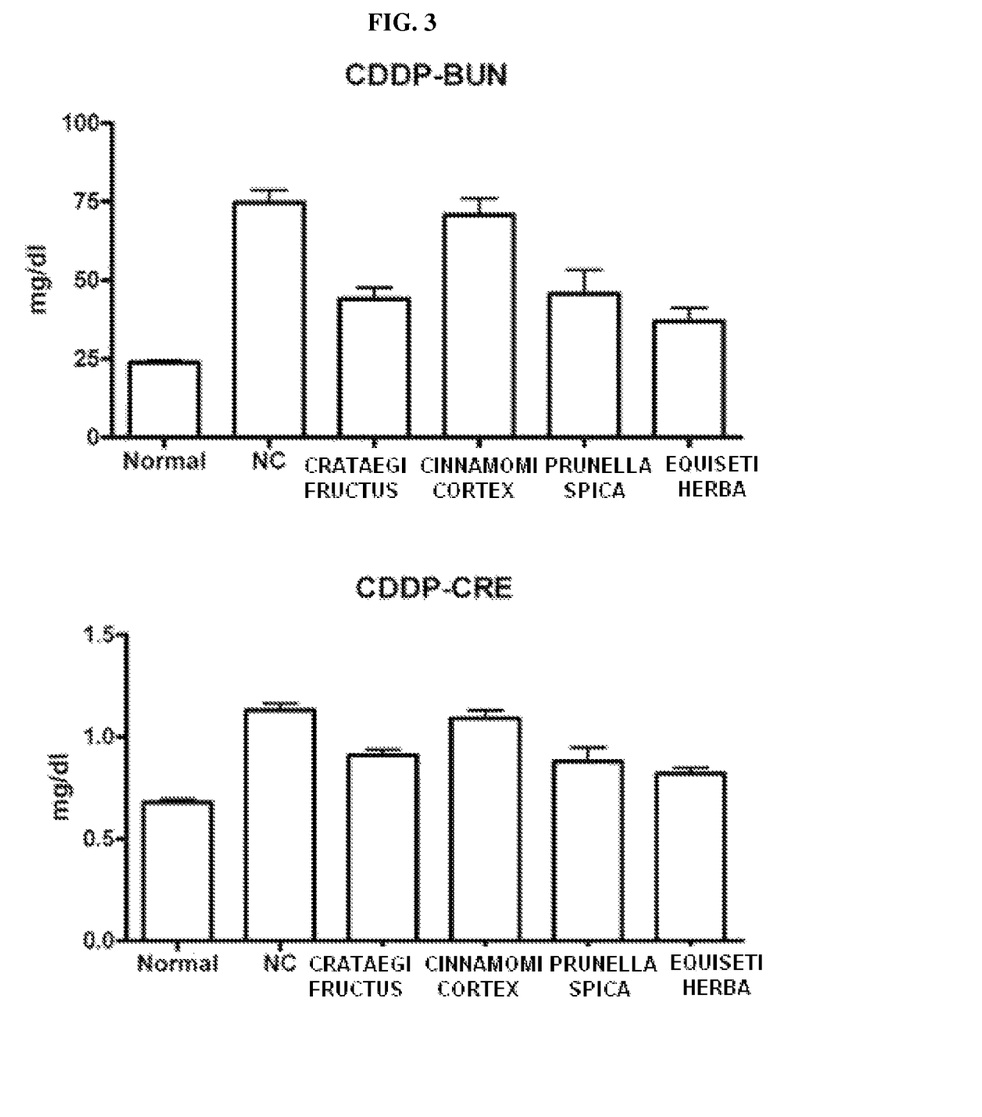
FIG. 3 shows the nephritis inhibitory activity of single herb extracts on a cisplatin-induced nephritis model.

Evaluation tests were conducted according to an evaluation method (Shirwaikar et al., *Journal of Ethnopharmacology* 90, 2004, 81-86) to investigate the therapeutic effect for nephritis of the single herb extracts of Example 1 and the mixtures of herbal extracts of Examples 3.1 to 3.11. The evaluation results for the single herb extracts of Example 1 are presented in FIG. 3 and Table 3, and the results for the mixtures of herbal extracts are in Table 3.

A normal group other than a positive control group was subjected to the tests, where a nephritis-inducing factor, cisplatin (purchased from Sigma) was administered intraperitoneally to male SD rats (7 weeks old, 195-205 g, Orient) at an injection dosage of 3 mg/kg for 3 days to induce nephritis. Among the test rats with induced nephritis, the test group other than the negative control group received the 4 test drugs (single herb extracts) of Example 1 and the 11 test drugs (mixtures of herbal extracts) of Examples 3 orally at a daily dosage of 400 mg/kg. The test rats were autopsied 7 days after the oral administrations. The blood samples collected were analyzed to measure the levels of blood urea nitrogen (B.U.N.) and creatinine.

TABLE 3

| Group | | Dosage (mg/kg) | B.U.N. (mg/dl) | Creatinine (mg/dl) |
|---|---|---|---|---|
| Example 1.1 | | 400 | 43.95 | 0.91 |
| Example 1.2 | | 400 | 70.75 | 1.09 |
| Example 1.3 | | 400 | 45.60 | 0.88 |
| Example 1.4 | | 400 | 36.84 | 0.82 |
| Example 3.1 | 10:1 | 400 | 48.42 | 0.90 |
| (Crataegi Fructus:Cinnamomi | 5:1 | 400 | 44.87 | 0.86 |
| Cortex) | 3:1 | 400 | 45.11 | 0.88 |
| | 1:1 | 400 | 53.58 | 0.93 |
| | 1:3 | 400 | 60.09 | 0.95 |
| | 1:5 | 400 | 64.08 | 0.99 |
| Example 3.2 | 10:1 | 400 | 43.15 | 0.90 |
| (Crataegi Fructus:Prunella | 5:1 | 400 | 41.47 | 0.83 |
| Spica) | 3:1 | 400 | 38.81 | 0.82 |
| | 1:1 | 400 | 40.94 | 0.83 |
| | 1:3 | 400 | 43.90 | 0.89 |
| | 1:5 | 400 | 45.14 | 0.90 |
| Example 3.3 | 10:1 | 400 | 34.11 | 0.79 |
| (Crataegi Fructus:Equiseti | 5:1 | 400 | 31.07 | 0.73 |
| Herba) | 3:1 | 400 | 30.72 | 0.71 |
| | 1:1 | 400 | 28.99 | 0.69 |
| | 1:3 | 400 | 28.71 | 0.67 |
| | 1:5 | 400 | 27.43 | 0.65 |
| Example 3.4 | 10:1 | 400 | 57.40 | 0.94 |
| (Cinnamomi Cortex:Prunella | 5:1 | 400 | 46.34 | 0.88 |
| Spica) | 4:1 | 400 | 45.19 | 0.88 |
| | 3:1 | 400 | 38.46 | 0.84 |
| | 1:1 | 400 | 30.11 | 0.69 |
| | 1:3 | 400 | 23.11 | 0.66 |
| | 1:5 | 400 | 39.85 | 0.83 |
| Example 3.5 | 7:1 | 400 | 40.71 | 0.87 |
| (Cinnamomi Cortex:Equiseti | 5:1 | 400 | 38.84 | 0.83 |
| Herba) | 3:1 | 400 | 33.97 | 0.73 |
| | 2:1 | 400 | 28.91 | 0.67 |
| | 1:1 | 400 | 30.75 | 0.71 |
| | 1:3 | 400 | 30.99 | 0.71 |
| | 1:5 | 400 | 32.59 | 0.75 |
| | 1:7 | 400 | 33.47 | 0.76 |
| Example 3.6 | 10:1 | 400 | 39.31 | 0.85 |
| (Prunella Spica:Equiseti | 5:1 | 400 | 37.71 | 0.82 |
| Herba) | 3:1 | 400 | 33.36 | 0.74 |
| | 1:1 | 400 | 34.01 | 0.74 |
| | 1:3 | 400 | 33.61 | 0.74 |
| | 1:5 | 400 | 32.86 | 0.73 |
| | 1:10 | 400 | 32.19 | 0.73 |
| Example 3.7 | 10:1:1 | 400 | 35.12 | 0.74 |
| (Crataegi Fructus:Cinnamomi | 2:2:3 | 400 | 34.81 | 0.74 |
| Cortex:Prunella | 1:1:5 | 400 | 33.98 | 0.73 |
| Spica) | | | | |
| Example 3.8 | 10:1:1 | 400 | 35.74 | 0.75 |

TABLE 3-continued

| Group | | Dosage (mg/kg) | B.U.N. (mg/dl) | Creatinine (mg/dl) |
|---|---|---|---|---|
| (Crataegi Fructus:Cinnamomi | 2:5:2 | 400 | 36.14 | 0.76 |
| Cortex:Equiseti | 1:1:5 | 400 | 32.83 | 0.74 |
| Herba) | | | | |
| Example 3.9 | 7:1:1 | 400 | 31.61 | 0.71 |
| (Crataegi Fructus:Prunella | 3:2:4 | 400 | 26.42 | 0.63 |
| Spica:Equiseti | 1:1:5 | 400 | 28.94 | 0.65 |
| Herba) | | | | |
| Example 3.10 | 7:1:1 | 400 | 42.79 | 0.83 |
| (Cinnamomi Cortex:Prunella | 3:2:5 | 400 | 33.65 | 0.67 |
| Spica:Equiseti | 1:1:7 | 400 | 32.57 | 0.65 |
| Herba) | | | | |
| Example 3.11 | 5:1:1:1 | 400 | 37.82 | 0.82 |
| (Crataegi Fructus:Cinnamomi | 3:2:2:2 | 400 | 31.10 | 0.71 |
| Cortex:Prunella | 1:1:1:5 | 400 | 32.88 | 0.72 |
| Spica:Equiseti | | | | |
| Herba) | | | | |
| Negative Control Group | | — | 74.74 | 1.13 |
| Normal Group | | — | 23.79 | 0.68 |

As can be seen from Table 3, as well as the single herb extracts of Examples 1.1 to 1.4, the mixtures of the herbal extracts of Examples 3.1 to 3.11 according to the defined compositions were all excellent in therapeutic effect for nephritis. In particular, the composition according to the mixing proportion of each ingredient that provides a good activity was determined, and the composite drugs containing Crataegi Fructus or Equiseti Herba had an overall good activity on the cisplatin-induced nephritis model, which was an acute nephritis model.

Experimental Example 5

Histopathological Investigation on Cisplatin-Induced Nephritis Model

From a test group of Experimental Example 4 treated with the 3:1, 1:1, or 1:3 mixture of the Cinnamomi Cortex extract and the Prunella Spica extract in Example 3.4, kidney tissues were harvested and subjected to histopathological investigation.

The kidney tissues harvested were formalin-fixed and cut into sections following a general tissue processing procedure. The kidney tissue sections were stained with hematoxylin and eosin and observed. Upon recognition of unusual histopathological findings, the severity of lesions was scored into four grades from minimal to marked severities.

Figure 4:
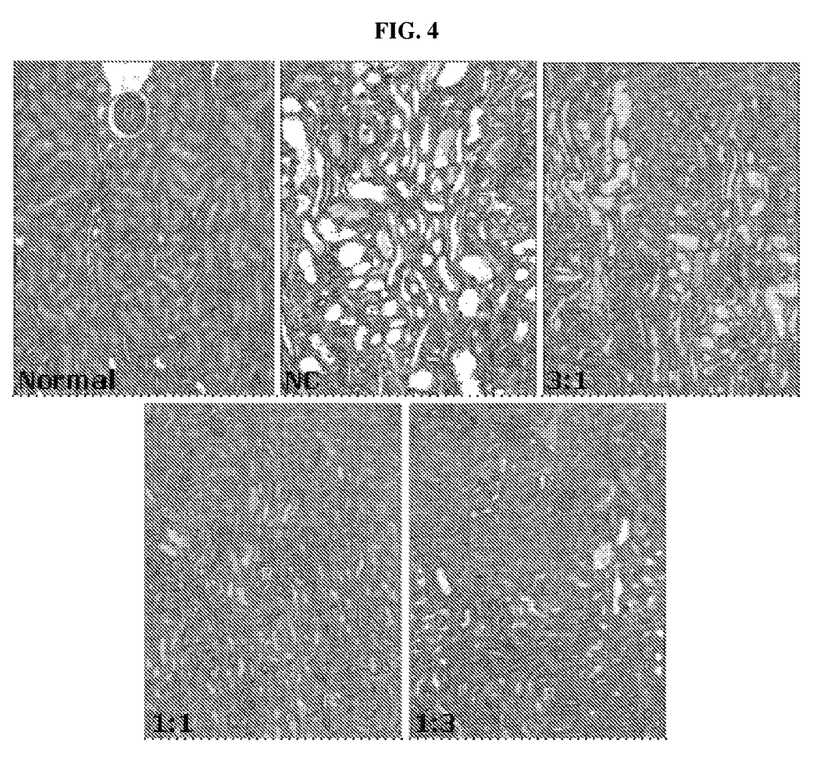
FIG. 4 shows the results of a histopathological investigation on the cisplatin-induced nephritis model.

The pathological changes of the kidney tissues are presented in FIG. 4 and Table 4.

TABLE 4

| | Organ: Kidney | | |
|---|---|---|---|
| Slide No. | Left-side | Right-side | Histopathological Findings |
| Normal Group | NM | NM | A) Tubular necrosis |
| Negative Control | A)1+, B)4+, C)2+, D)1+, E)2+, F)1+ | A)1+, B)3+, C)2+, E)2+, F)1+ | B) Tubular regeneration C) Tubular dilation |
| Example 3.4  3:1 | A)1+, B)4+, C)1+, E)1+ | A)1+, B)3+, C)1+ | D) Hyaline cast E) Interstitial inflammation |
| 1:1 | A)1+, B)4+, C)1+ | A)1+, B)3+ | F) Interstitial fibrosis |
| 1:3 | A)1+, B)1+, C)1+ | A)1+, B)2+ | NM) No microscopic findings 1+: Minimal 2+: Mild 3+: Moderate 4+: Marked |

In the normal group of FIG. 4, where G is glomeruli and T is renal tubules, there was no noticeable lesion in regard to nephritis. In the negative control group of FIG. 4, the kidney tissue had minimal tubular necrosis and marked tubular regeneration. Other findings were tubular dilation, interstitial inflammation, hyaline casts, and interstitial fibrosis. The group treated with the test drugs had slight lesions relative to those in the negative control group, such as of tubular necrosis, tubular regeneration and tubular dilation, but neither hyaline casts nor interstitial fibrosis was recognized in the test group.

In contrast to the negative control group, the test group demonstrated the therapeutic effect for nephritis according to the histopathological observation. Particularly, as can be seen from Table 4, the 1:3 mixture of Example 3.4 was superior in activity to the 3:1 or 1:1 mixture.

Experimental Example 6

Test of Therapeutic Effect on Cyclosporine A-Induced Nephritis Model

Activity tests were conducted according to an evaluation method (So Young Lee et al., *Experimental transplantation* 78, 2004, 1756-1764) to evaluate the therapeutic effect for chronic nephritis of the 3:1, 1:1 and 1:3 mixtures of herbal extracts in Examples 3.1, 3.3, 3.4, and 3.5.

A normal group other than a positive control group was subjected to the tests, where a nephritis-inducing factor, cyclosporine A (CsA, purchased from Chong Kun Dang Pharm. Corp.) was administered intraperitoneally to male SD rats (7 weeks old, 195-205 g, Orient) at an injection dosage of 50 mg/kg for 8 weeks to induce nephritis. Among the test rats with induced nephritis, the test group other than the negative control group received the 3:1, 1:3 and 1:3 mixtures of herbal extracts of Examples 3.1, 3.3, 3.4, and 3.5 orally at a daily dosage of 400 mg/kg 3 days before the administration of cyclosporine A. The test rats were autopsied 8 weeks after the induction of nephritis, and the blood samples collected were analyzed to measure the levels of blood urea nitrogen (B.U.N.) and creatinine.

TABLE 5

| Group | | Dosage (mg/kg) | B.U.N. (mg/dl) | Creatinine (mg/dl) |
|---|---|---|---|---|
| Example 3.1 | 3:1 | 400 | 42.1 | 0.73 |
| | 1:1 | 400 | 40.4 | 0.73 |
| | 1:3 | 400 | 37.8 | 0.73 |
| Example 3.3 | 3:1 | 400 | 34.1 | 0.68 |
| | 1:1 | 400 | 39.4 | 0.75 |
| | 1:3 | 400 | 43.9 | 0.74 |
| Example 3.4 | 3:1 | 400 | 37.0 | 0.73 |
| | 1:1 | 400 | 34.3 | 0.68 |
| | 1:3 | 400 | 30.5 | 0.62 |
| Example 3.5 | 3:1 | 400 | 35.2 | 0.71 |
| | 1:1 | 400 | 39.1 | 0.72 |
| | 1:3 | 400 | 42.3 | 0.73 |
| Negative Control Group | | — | 61.6 | 1.02 |
| Normal Group | | — | 21.5 | 0.54 |

As can be seen from Table 5, the negative control group and the test groups treated with cyclosporine A had an increase in the levels of B.U.N. and creatinine relative to the normal group, but all the treated groups in contrast to the negative control group had a significant decrease in the levels of B.U.N. and creatinine. In particular, the 1:3 mixture of the Cinnamomi Cortex extract and the Prunella Spica extract in Example 3.4 was most excellent in activity on the cyclosporine A-induced nephritis model, which was a chronic nephritis model.

Experimental Example 7

Test of Therapeutic Effect on Cisplatin-Induced Nephritis Model

To evaluate the therapeutic effect for nephritis of the 3:1, 1:1 and 1:3 mixtures of herbal extracts in Example 3.4, which showed a good result of evaluation above, on a cisplatin-induced nephritis model, evaluation tests were conducted according to an evaluation method (Shirwaikar et al., *Journal of Ethnopharmacology* 90, 2004, 81-86).

A normal group other than a positive control group was subjected to the tests, where a nephritis-inducing factor, cisplatin was administered intraperitoneally to the test group at an injection dosage of 3 mg/kg for 3 days (refer to Experimental Example 4). The test group other than the negative control group received the 3:1, 1:1 and 1:3 mixtures of herbal extracts in Example 3.4 orally at daily dosages of 100, 200 and 400 mg/kg. The test rats were autopsied 7 days after the oral administrations. The blood samples collected were analyzed to measure the levels of blood urea nitrogen (B.U.N.) and creatinine. The results are presented in Table 6.

TABLE 6

| Group | | Dosage (mg/kg) | B.U.N. (mg/dl) | Creatinine (mg/dl) |
|---|---|---|---|---|
| Example 3.4 | 3:1 | 100 | 42.12 | 0.87 |
| | | 200 | 40.79 | 0.85 |
| | | 400 | 37.87 | 0.84 |
| | 1:1 | 100 | 34.65 | 0.75 |
| | | 200 | 31.71 | 0.73 |
| | | 400 | 29.77 | 0.70 |
| | 1:3 | 100 | 31.51 | 0.74 |
| | | 200 | 25.14 | 0.67 |
| | | 400 | 23.89 | 0.67 |
| Negative Control Group | | — | 79.51 | 1.14 |
| Normal Group | | — | 22.46 | 0.65 |

As can be seen from Table 6, all the test drugs with different mixing ratios in Example 3.4 showed a good therapeutic effect for nephritis. In particular, the 1:3 mixture of the Cinnamomi Cortex extract and the Prunella Spica extract was most excellent in activity.

Experimental Example 8

Cytotoxicity Testing for Rat Kidney Mesangial Cells

To evaluate the 4 single herb extracts of Example 1 and the 11 mixtures of herbal extracts in Example 3 in regard to cytotoxicity for kidney mesangial cells, evaluation tests were conducted according to an evaluation method (R. Wang et al., *Life Sciences* 80, 2007, 2481-2488). The evaluation results for the single herb extracts of Example 1 and the mixtures of herbal extracts of Example 3 are presented in Table 7.

For the 4 single herb extracts of Example 1 and the 11 mixtures of Example 3, each 10 mg was dissolved in an appropriate amount of DMSO to prepare a sample with the final concentration of 40 mg/ml. Mesangial cells cultured in a 96-well plate ($1 \times 10^4$, 24 hours) were treated with the sample at a maximum concentration of 400 μg/ml with a common ratio of 2. After 24 hours of culture, the medium was replaced with another one containing 0.5 mg/ml of MTT. After an elapse of 4 more hours, the medium was discarded, and 100 μl of DMSO was added to each cell. In 15 minutes, absorbance at 540 nm was measured to determine the toxicity on the mesangial cells.

TABLE 7

| Group | | $IC_{50}$(μg/ml) |
|---|---|---|
| Example 1.1 | | 338.8 |
| Example 1.2 | | 309.1 |
| Example 1.3 | | 288.4 |
| Example. 1.4 | | 218.2 |
| Example 3.1 | 10:1 | 321.2 |
| (Crataegi Fructus:Cinnamomi | 5:1 | 308.3 |
| Cortex) | 1:5 | 307.9 |
| Example 3.2 | 10:1 | 319.7 |
| (Crataegi Fructus:Prunella | 3:1 | 296.5 |
| Spica) | 1:3 | 275.8 |
| Example 3.3 | 10:1 | 305.7 |
| (Crataegi Fructus:Equiseti | 5:1 | 284.8 |
| Herba) | 1:5 | 258.8 |
| Example 3.4 | 10:1 | 327.4 |
| (Cinnamomi Cortex:Prunella | 4:1 | 300.1 |
| Spica) | 1:5 | 272.5 |
| Example 3.5 | 7:1 | 273.6 |
| (Cinnamomi Cortex:Equiseti | 2:1 | 244.8 |
| Herba) | 1:7 | 218.1 |
| Example 3.6 | 10:1 | 263.7 |
| (Prunella Spica:Equiseti | 3:1 | 224.3 |
| Herba) | 1:10 | 201.8 |
| Example 3.7 | 10:1:1 | 314.9 |
| (Crataegi Fructus:Cinnamomi | 2:2:3 | 305.4 |
| Cortex:Prunella | 1:1:5 | 289.7 |
| Spica) | | |
| Example 3.8 | 10:1:1 | 302.4 |
| (Crataegi Fructus:Cinnamomi | 2:5:2 | 283.1 |
| Cortex:Equiseti | 1:1:5 | 232.8 |
| Herba) | | |
| Example 3.9 | 7:1:1 | 289.3 |
| (Crataegi Fructus:Prunella | 3:2:4 | 258.9 |
| Spica:Equiseti | 1:1:5 | 216.4 |
| Herba) | | |
| Example 3.10 | 7:1:1 | 274.9 |
| (Cinnamomi Cortex:Prunella | 3:2:5 | 219.4 |
| Spica:Equiseti | 1:1:7 | 204.3 |
| Herba) | | |
| Example 3.11 | 5:1:1:1 | 301.9 |
| (Crataegi Fructus:Cinnamomi | 3:2:2:2 | 270.1 |
| Cortex:Prunella | 1:1:1:5 | 218.9 |
| Spica:Equiseti | | |
| Herba) | | |

As can be seen from Table 7, as well as the 4 single herb extracts of Examples 1, the 11 mixtures of herbal extracts with different compositions in Example 3 were all excellent in inhibitory effect on the growth of the kidney mesangial cells. In particular, an ingredient-based mixing proportion for good activity was determined, and Prunella Spica, Equiseti Herba, or a composite drug containing Prunella Spica and Equiseti Herba had an overall good inhibitory activity on the growth of kidney mesangial cells.

Example 9

Active Fraction and Ingredient Identification of Herbal Extract

To achieve active fraction and ingredient identification of herbal extracts, an activity-guided sub-fractionation was conducted by way of a mouse ear edema inhibition test.

Each herbal extract of Example 1 was suspended in a volume of distilled water 2 to 10 times the weight of the extract and then subjected to 2 to 3 sequential solvent fractionations using methylene chloride (MC), ethylene acetate (EA) and butanol (BuOH) in a volume (v/v) 2 to 5 times the suspended extract. The active fraction thus obtained was pattern-analyzed with HPLC. To identify the active ingredients of the fraction, the MC fraction of the extract of Example 1.2 was subjected to silica gel column chromatography using a mixed solvent of hexane and EA (10:1 to 1:10, v/v) and Sephadex LH-20 column chromatography using MeOH as a solvent to isolate compounds 1 and 2. The BuOH fraction of the extract of Example 1.3 was subjected to C18 column chromatography using 60% MeOH as a solvent and Sephadex LH-20 column chromatography using a mixed solvent of $CH_2Cl_2$ and MeOH (1:1, v/v) to isolate a compound 3. The compounds isolated were identified through an instrumental analysis with LC-MS/MS, $^1$H-NMR, $^{13}$C-NMR, UV spectrometer, etc. and in reference to documents. The results are presented in Table 8.

TABLE 8

| Div. | Ingredient |
|---|---|
| Compound 1 | Cinnamic acid |
| Compound 2 | Coumarin |
| Compound 3 | Rosmarinic acid |

The identification data are as follows:

Cinnamic acid: White powder.

$^1$H-NMR (250 MHz, CDCl3): δ 7.79 (1H, d, J=16 Hz, H-7), 7.56 (2H, m, H-2, 6), 7.40 (3H, m, H-3, 4, 5), 6.45 (1H, d, J=16 Hz, H-8); $^{13}$C-NMR (63 MHz, $CDCl_3$): δ 173.2 (C-9), 147.6 (C-7), 134.4 (C-1), 131.2 (C-4), 129.4 (C-3, 5), 128.8 (C-2, 6), 117.7 (C-8)

Coumarin: White powder.

$^1$H-NMR (250 MHz, CD3OD): δ 7.89 (1H, d, J=9.6 Hz, H-4), 7.51-7.58 (2H, m, H-5, 7), 7.25-7.31 (2H, m, H-6, 8), 6.46 (1H, d, J=9.6 Hz, H-3); $^{13}$C-NMR (63 MHz, $CD_3OD$): δ 162.7 (C-2), 155.2 (C-9), 145.6 (C-4), 133.1 (C-7), 129.4 (C-5), 125.8 (C-6), 120.3 (C-10), 117.5 (C-3), 117.1 (C-8)

Rosmarinic acid: Yellowish amorphous powder.

$^1$H-NMR (250 MHz, DMSO): δ 7.46 (1H, d, J=16.0 Hz, H-7), 7.05 (1H, d, J=2.0 Hz, H-2), 7.00 (1H, dd, J=8.0, 2.0 Hz, H-6), 6.76 (1H, d, J=8.0 Hz, H-5), 6.67 (1H, d, J=2.0 Hz, H-2'), 6.63 (1H, d, J=8.0 Hz, H-5'), 6.52 (1H, dd, J=8.0, 2.0 Hz, H-6'), 6.23 (1H, d, J=16.0 Hz, H-8), 5.02 (1H, m, H-8'), 2.99 (1H, m, H-7'b), 2.90 (1H, m, H-7'a); $^{13}$C-NMR (63 MHz, DMSO): δ 170.7 (C-9'), 165.8 (C-9), 148.5 (C-4), 145.8 (C-7), 145.5 (C-3), 144.8 (C-3'). 143.9 (C-4'), 127.2 (C-1'), 125.3 (C-1), 121.5 (C-6), 120.0 (C-6'), 116.6 (C-2'), 115.7 (C-5'), 115.3 (C-5), 114.8 (C-8), 113.2 (C-2), 72.7 (C-8'), 36.1 (C-7')

To evaluate the edema inhibitory effects of the MC, EA and BuOH fractions from the herbal extracts of Examples 1.2 and 1.3 and the three compounds identified above, an activity test was conducted according to a method by Hee Kee Kim et al. [Hee Kee Kim et al., *Arch. Pharm. Res.* 16(1), 1993, 18-24].

The positive control group received Indomethacin (purchased from Sigma) at a dosage of 20 mg/kg. The test group received 200 mg/kg of the MC, EA or BuOH fraction, or 20 mg/kg of the compound 1, 2 or 3.

One hour after the oral administration, 2.5% croton oil (purchased from Sigma) was applied to the one ear of a male ICR mouse (7 weeks old, 28-32 g, Orient) to induce an acute inflammation. In 4 hours, the swelling of the ear was measured in terms of thickness. The results are presented in Table 9.

TABLE 9

| Div. | | Dosage (mg/kg) | % Inhibition |
| --- | --- | --- | --- |
| Example 1.2 | MC Fraction | 200 | 31.54 |
| | EA Fraction | 200 | 2.70 |
| | BuOH Fraction | 200 | 4.64 |
| Example 1.3 | MC Fraction | 200 | 3.68 |
| | EA Fraction | 200 | 30.64 |
| | BuOH Fraction | 200 | 40.85 |
| | Compound 1 | 20 | 42.40 |
| | Compound 2 | 20 | 38.79 |
| | Compound 3 | 20 | 28.90 |
| Positive Control Group | | 20 | 38.81 |

As can be seen from Table 9, the positive control group showed 39% inhibition on the acute inflammation induced by croton oil, and the MC fraction of Example 1.2 and the EA and BuOH fractions of Example 1.3 showed more than 30% significant inhibition. The three compounds were also effective in inhibition of the acute inflammation. The compounds 1 and 2, for example, showed a high inhibitory activity of 42% and 39%, respectively.

Experimental Example 10

Test of Therapeutic Effect on Gentamicin-Induced Nephritis Model

To evaluate the therapeutic effect for nephritis of the three compounds of Experimental Example 9, the procedures were carried out in the same manner of Experimental Example 1 to measure the B.U.N and creatinine contents in the gentamicin-induced nephritis model. Reagents were the compounds 1, 2 and 3, which were the active fractions from the herbal extracts of Cinnamomi Cortex and Prunella Spica. The results are presented in Table 10.

TABLE 10

| Div. | Dosage (mg/kg) | B.U.N. (mg/dl) | Creatinine (mg/dl) |
| --- | --- | --- | --- |
| Compound 1 | 20 | 47.7 ± 5.7*** | 0.81 ± 0.07* |
| Compound 2 | 20 | 50.9 ± 4.7** | 0.88 ± 0.06 |
| Compound 3 | 20 | 63.1 ± 7.2 | 0.97 ± 0.06 |
| Negative Control Group | — | 83.0 ± 5.1 | 1.32 ± 0.12 |
| Normal Group | — | 12.4 ± 0.6 | 0.45 ± 0.01 |

*$P < 0.05$,
**$P < 0.01$,
***$P < 0.001$
(relative to negative control group)

As shown in Table 10, among the ingredients of the mixture of the Cinnamomi Cortex extract and the Prunella Spica extract, cinnamic acid and coumarin showed an effect of reducing the blood urea nitrogen (B.U.N.) content in the gentamicin-induced nephritis model with a statistical significance relative to the negative control group. Cinnamic acid also reduced the creatinine content and had the highest activity of improving the nephritis symptoms.

Hereinafter, a description will be given as to exemplary formulations of the composition comprising the extract of the present invention, which are given only for illustrative purposes and not intended to limit the scope of the present invention.

Formulation Example 1

Preparation of Powder Formulation

| | |
| --- | --- |
| Extracts of Examples 1 to 3 | 80 mg |
| Lactose | 100 mg |
| Talc | 10 mg |

The above ingredients were blended together and packed in an air tight pouch.

Formulation Example 2

Preparation of Tablet Formulation

| | |
| --- | --- |
| Extracts of Examples 1 to 3 | 100 mg |
| Corn starch | 100 mg |
| Lactose | 100 mg |
| Magnesium stearate | 2 mg |

The above ingredients were blended together and formed into tablets according to a traditional tabletting method.

Formulation Example 3

Preparation of Capsule Formulation

| | |
| --- | --- |
| Extracts of Examples 1 to 3 | 100 mg |
| Crystalline cellulose | 3 mg |
| Lactose | 14.8 mg |
| Magnesium stearate | 0.2 mg |

The above ingredients were blended together and packed in gelatin capsules according to a traditional preparation method for capsules.

Formulation Example 4

Preparation of Injectable Formulation

| | |
| --- | --- |
| Extracts of Examples 1 to 3 | 10 mg |
| Mannitol | 180 mg |
| Sterile distilled water for injection | 2974 mg |
| $Na_2HPO_4 \cdot 12H_2O$ | 100 mg |

The ingredients were used in the above contents per ample (2 ml) according to a traditional preparation method for injectable formulations.

Formulation Example 5

Preparation of Solution Formulation

| | |
|---|---|
| Extracts of Examples 1 to 3 | 20 mg |
| High fructose corn syrup | 10 g |
| Mannitol | 5 g |
| Purified water | appropriate amount |

According to a traditional preparation method for solution formulations, the individual ingredients were dissolved in purified water and, after addition of lemon flavor, mixed together. An appropriate amount of purified water was added to the mixture to make the solution 100 ml in total volume. The solution was filled in a dark bottle and sterilized to prepare a solution preparation.

Formulation Example 6

Preparation of Health Functional Food

| | |
|---|---|
| Extracts of Examples 1 to 3 | 1000 mg |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 μg |
| Nicotinic acid amide | 1.7 mg |
| Folic acid | 50 μg |
| Calcium pantothenic acid | 0.5 mg |
| Mineral mixture | appropriate amount |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

The composition of the vitamin-mineral mixture as described herein was prepared by mixing ingredients relatively appropriate for health functional foods at a mixing ratio according to a preferred example, but the mixing ratio of the ingredients may be modified without any limitations. According to a traditional preparation method for health functional foods, all the ingredients are blended together and formed into granules, which may be used for a preparation of health functional foods by a traditional method.

Formulation Example 7

Preparation of Health Functional Beverage

| | |
|---|---|
| Extracts of Examples 1 to 3 | 1000 mg |
| Citric acid | 1000 mg |
| Oligosaccharide | 100 mg |
| *Prunus mume* juice concentrate | 2 g |
| Taurine | 1 g |
| Total volume with purified water | 900 ml |

According to a traditional preparation method for health functional beverages, all the ingredients were blended together and heated under agitation at 80° C. for about 1 hour. The solution thus obtained was filtered and poured in a sterile 2 L container, which was seal-sterilized, kept in a refrigerator and used to prepare a composition for health functional beverage according to the present invention.

The composition as described herein was prepared by mixing ingredients relatively appropriate for beverages at a mixing ratio according to a preferred example, but the mixing ratio of the ingredients may be modified according to geographic and ethnic preferences, such as target customers, target country, usage, etc.

The invention claimed is:

1. A method for treating nephritis in a human in need thereof consisting essentially of administering therapeutically effective amounts of an extract selected from the group consisting of a Cinnamomi Cortex extract, a Prunella Spica extract, an Equiseti Herba extract and a mixture of two or more of the extracts; or
   a mixture of Crataegi Fructus extract and an extract selected from the group consisting of a Cinnamomi Cortex extract, a Prunella Spica extract, an Equiseti Herba extract and a mixture of two or more of the extracts,
   to the human in need thereof to treat the nephritis.

2. The method as claimed in claim 1, wherein the extract is prepared by extraction with water, a C1-C6 alcohol, an aqueous C1-C6 alcohol solution, or a mixture thereof.

3. The method as claimed in claim 2, wherein the concentration of the aqueous C1-C6 alcohol solution is 10 to 90% (v/v).

4. The method as claimed in claim 1, wherein the extract is selected from the group consisting of:
   a mixture of the Crataegi Fructus extract and the Cinnamomi Cortex extract at a weight ratio of 10:1 to 1:5; a mixture of the Crataegi Fructus extract and the Prunella Spica extract at a weight ratio of 10:1 to 1:5; a mixture of the Crataegi Fructus extract and the Equiseti Herba extract at a weight ratio of 10:1 to 1:5; a mixture of the Cinnamomi Cortex extract and the Prunella Spica extract at a weight ratio of 10:1 to 1:5; a mixture of the Cinnamomi Cortex extract and the Equiseti Herba extract at a weight ratio of 7:1 to 1:7; a mixture of the Prunella Spica extract and the Equiseti Herba extract at a weight ratio of 10:1 to 1:10; a mixture of the Crataegi Fructus extract, the Cinnamomi Cortex extract, and the Prunella Spica extract at a weight ratio of 10:1:1 to 1:1:5; a mixture of the Crataegi Fructus extract, the Cinnamomi Cortex extract, and the Equiseti Herba extract at a weight ratio of 10:1:1 to 1:1:5; a mixture of the Crataegi Fructus extract, the Prunella Spica extract, and the Equiseti Herba extract at a weight ratio of 7:1:1 to 1:1:5; a mixture of the Cinnamomi Cortex extract, the Prunella Spica extract, and the Equiseti Herba extract at a weight ratio of 7:1:1 to 1:1:7; and a mixture of the Crataegi Fructus extract, the Cinnamomi Cortex extract, the Prunella Spica extract, and the Equiseti Herba extract at a weight ratio of 5:1:1:1 to 1:1:1:5.

5. The method as claimed in claim 1, wherein the nephritis is selected from the group consisting of glomerulonephritis, pyelonephritis, interstitial nephritis, lupus nephritis, diabetic nephropathy, proteinuria, tubular atrophy, glomerulosclerosis, and renal failure.

6. The method as claimed in claim 1, wherein the extract is administered at a daily dosage of 0.7 to 500 mg/kg to said human.

* * * * *